United States Patent [19]

Freitag

[11] 3,957,569
[45] May 18, 1976

[54] APPARATUS FOR SEVERING AND SEALING THE ENDS OF A MULTI-PLY PAD

[75] Inventor: Ludwig W. Freitag, Elkhart Lake, Wis.

[73] Assignee: Curt G. Joa, Inc., Sheboygan Falls, Wis.

[22] Filed: Jan. 27, 1975

[21] Appl. No.: 544,548

[52] U.S. Cl. ............... 156/515; 156/518; 156/582; 93/33 R
[51] Int. Cl.² ............ B32B 31/18; B32B 31/20
[58] Field of Search .......... 156/515, 251, 518, 530, 156/582, 583, 555, 510; 93/33 H, 33 R, 8 R, DIG. 1; 53/39, 373

[56] References Cited
UNITED STATES PATENTS

| | | | |
|---|---|---|---|
| 2,686,556 | 8/1954 | Gerber et al. | 156/515 |
| 3,033,257 | 5/1962 | Weber | 156/515 |
| 3,083,757 | 4/1963 | Kraft et al. | 156/251 |

Primary Examiner—William A. Powell
Assistant Examiner—M. G. Wityshyn
Attorney, Agent, or Firm—Joseph P. House, Jr.

[57] ABSTRACT

A multi-ply pad, such as a disposable diaper, is cut from a series of interconnected pads by a combined severing and sealing tool having a knife blade which severs through the multi-ply links on which the pads are serially interconnected. The knife edge is immediately followed by a blunt heel which seals the multiple plies of sheet material together. Accordingly, when the separated pads are sequentially handled to be folded, the multiple plies at one end of the pad will not flare or otherwise become disoriented with respect to each other and to the pad. This greatly facilitates and simplifies handling of the pads after they are severed.

2 Claims, 6 Drawing Figures

APPARATUS FOR SEVERING AND SEALING THE ENDS OF A MULTI-PLY PAD

BACKGROUND OF THE INVENTION

Heretofore, serially linked multi-ply disposable pads such as diapers are separated one from another by the act of severing through the multi-ply links. This loosens the plies at the cut edge. Accordingly, when the pad is further handled, for example, to fold it over, the loose ends of the pad plies tend to flare out or otherwise become disoriented with respect to each other and to the pad. This militates against a neat folded pad and complicates packaging the pads in a neat arrangement.

SUMMARY OF THE INVENTION

In accordance with the present invention, the leading multi-ply edge of each pad severed from a series of interconnected pads has the multiple plies adjacent the cut line sealed together so that these multiple plies will not flare out or otherwise become disoriented when the pad is subsequently folded or otherwise manipulated, for example, in the course of packaging it. For this purpose the tool which severs through the multi-ply links interconnecting successive pads is provided both with a knife edge and an adjacent following blunt heel. The knife edge coacts with the pad links to sever therethrough and substantially concurrently the heel will pressure seal the multiple plies together to prevent flaring and to hold these plies together in proper orientation during subsequent folding or other manipulation of the pad.

The blunt sealing heel on the tool desirably comprises a flat portion which is disposed at such an angle to the radius of the knife rotor that it will be substantially parallel to a tangent to the anvil rotor in the sealing position of the tool.

By combining the knife edge and the sealing bar in a single tool, both the severing and the sealing operation are carried out substantially at the same time, thus simplifying the apparatus and speeding production.

Other objects, features and advantages of the invention will appear from the disclosure hereof.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

Figure 3:
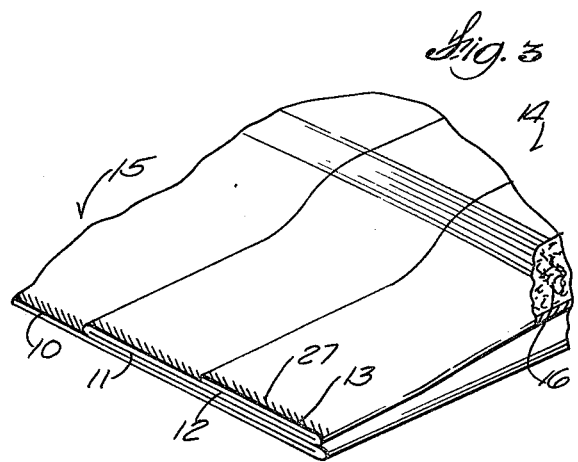
FIG. 3 is a fragmentary perspective view showing the leading edge of a pad after it has been severed and sealed in accordance with the present invention.

As shown in FIG. 3 hereof, a typical multi-ply disposable pad 14, such as a diaper, comprises multiple layers 10, 11, 12 and 13 of sheet material. These multiple layers 10–13 come into juxtaposition at the extending tabs or links 15 of serially interconnected pads. The body of the pad 14 typically includes a fluff filler 16, the pads 14 being much thicker in the area of the filler 16 than in the area of the tab ends or links 15.

Figure 5:
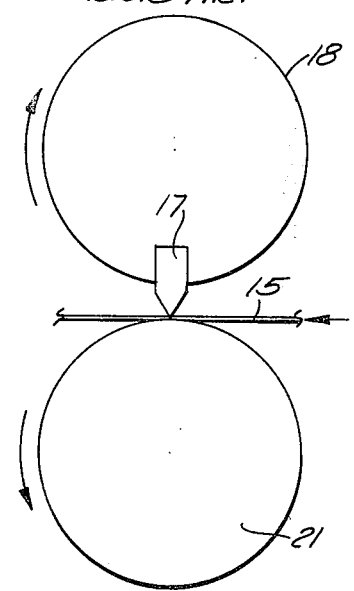
FIG. 5 is a diagrammatic view illustrating the prior art.

In the prior art severing technique illustrated in FIG. 5, the links of such serially interconnected diaper pads 14 are severed by a knife 17 mounted on a knife rotor 18. The knife 17 coacts with an anvil rotor 21. The disadvantage of the prior art apparatus is that after severing through the links 15, the multiple plies 10–13 aforesaid are loose or free of interconnection at the cut edge. During subsequent manipulation of the pad, these plies tend to separate and flare out, thus making it difficult to control and handle the pad during packaging.

Figure 1:
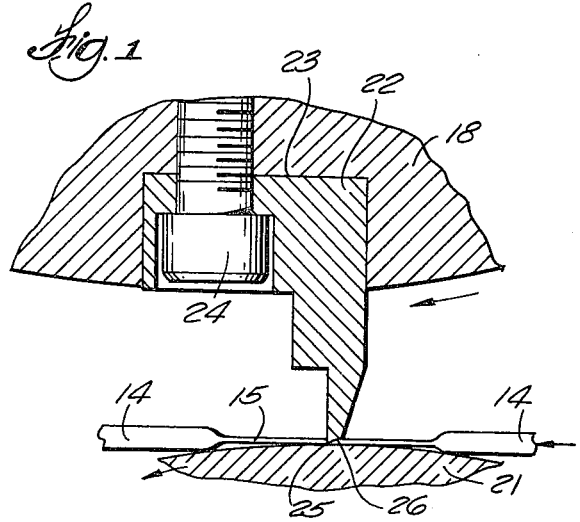
FIG. 1 is a fragmentary cross section taken through the knife and anvil rotors and the tool embodying the present invention. This figure illustrates the severing position of the parts.
Figure 2:
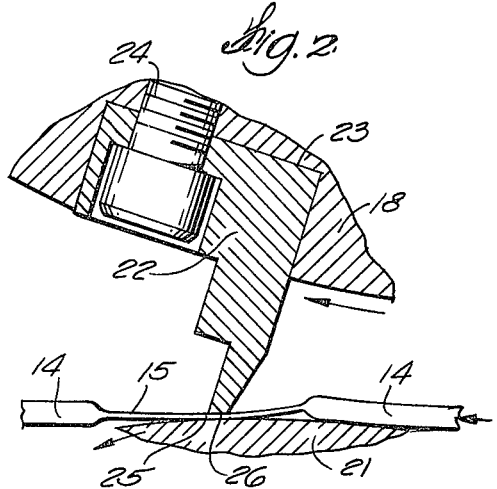
FIG. 2 is a view similar to FIG. 1 but in which the rotors have moved slightly beyond the severing position and are in their sealing position.
Figure 6:
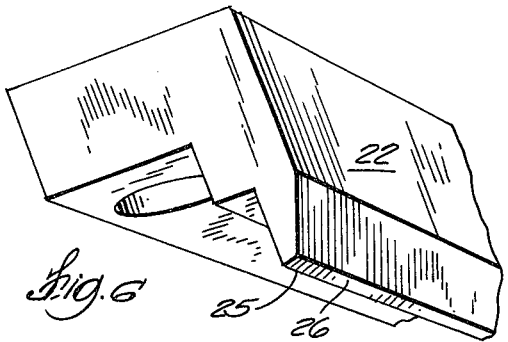
FIG. 6 is a fragmentary perspective view of the combined severing and sealing tool.

In accordance with the present invention, the knife 17 of the prior art is replaced by a combined severing and sealing tool 22. As illustrated in FIGS. 1, 2 and 6, the tool comprises a bar held into a suitable socket 23 in the knife rotor 18 by bolts 24. the leading edge of the tool is provided with a knife edge 25 and is followed by a blunt sealing heel 26. Heel 26 is desirably flat and is disposed at approximately a 70° angle to a radial line through the axis of rotation of the knife roll 18 and the knife edge 25. Accordingly, when the parts are in the severing position shown in FIG. 1, heel 26 is at approximately a 20° angle to a tangent to the anvil roller 21 at the point of contact of knife edge 25 therewith. This angle may vary somewhat, depending upon the dimension of the parts, for example, the size of the rotors 18, 21.

In the severing position of the tool 22 as shown in FIG. 1, the sharp knife edge 25 has severed through the multiply layers 10–13 of the link 15. Continued rotation of the rotors 18, 21 will bring the parts to their sealing position of FIG. 2 in which the flat blunt heel 26 comes into parallelism with a tangent to the anvil roller 21 at the point of contact of knife edge 25 therewith. Sealing pressure between the heel 26 and the anvil 21 will seal the plies 10–13, inclusive, in a narrow band 27 immediately adjacent the cut line through the link 15. Seal 27 is effectuated entirely by pressure and without the need for any binders or adhesives. The pressure embosses or knits the sheet material together in a releasable bond which can be disrupted with relatively minor effort, but which will hold together during normal subsequent handling of the pad.

Figure 4:
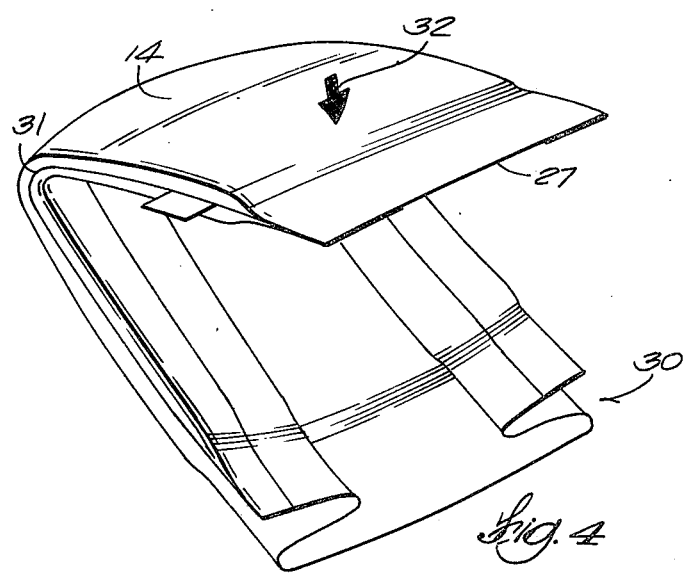
FIG. 4 is a perspective view diagrammatically illustrating the act of folding a pad having its leading edge severed and sealed in accordance with the present invention and in which flare is prevented.

Seal 27 is impressed only at the leading edge of the pads 14. The trailing edge is not subject to sealing pressure and is left loose as illustrated at 30 in FIG. 4. FIG. 4 illustrates how the plies at the trailing edge 30 can separate and tend to flare out in the absence of the bond.

However, it is not disadvantageous that the trailing edge of the pad 14 is unsealed because during subseqent handling of the pad 14 only the leading edge is normally subjected to such forces as would tend to flare the ply ends and otherwise disorient the ply ends. FIG. 4 illustrates how a pad 14 is typically folded about its transverse bight 31 in the direction of arrow 32. While the pad is being thus folded or flipped over itself, the plies at its leading edge are held together by the sealing band 27 and will not flare or become otherwise disoriented.

What is claimed is:

1. Severing and sealing apparatus for a multi-ply pad, said apparatus comprising coacting knife and anvil rotors, a combined severing and sealing tool, means mounting said tool on the knife rotor, said tool comprising an elongated blade having a knife edge at the leading edge of said blade in the direction of its rotation and which coacts with the anvil rotor for severing through the multiple plies of a pad therebetween and a blunt sealing heel adjacent said knife edge at the trailing edge of said blade in the direction of its rotation and which coacts with the anvil rotor for sealing together said multiple plies adjacent the line of severance therethrough substantially concurrently with the severing thereof, said anvil rotor having a substantially smooth cylindrical surface, said heel having a substantially flat portion disposed at an acute angle to a radial line through the axis of rotation of the knife rotor and the point of contact of the knife edge with the pad such that said flat portion will be substantially parallel to a tangent to said cylindrical surface at said point of contact in the sealing position thereof.

2. The apparatus of claim 1 in which said heel is at approximately a 70° angle to said radial line.

* * * * *